United States Patent
Myhre et al.

(10) Patent No.: US 8,878,133 B2
(45) Date of Patent: Nov. 4, 2014

(54) PASSIVE OPTICAL GASEOUS EMISSIONS SENSOR

(75) Inventors: Douglas C. Myhre, Eden Prairie, MN (US); Odd Harald S. Eriksen, Minneapolis, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 475 days.

(21) Appl. No.: 13/267,526

(22) Filed: Oct. 6, 2011

(65) Prior Publication Data

US 2012/0105828 A1    May 3, 2012

Related U.S. Application Data

(60) Provisional application No. 61/409,294, filed on Nov. 2, 2010.

(51) Int. Cl.
*G01N 21/35*    (2014.01)
*G01N 21/85*    (2006.01)
*G01N 21/55*    (2014.01)

(52) U.S. Cl.
CPC .......... *G01N 21/3504* (2013.01); *G01N 21/554* (2013.01); *G01N 21/8507* (2013.01)
USPC .................................. 250/338.5; 250/339.13

(58) Field of Classification Search
USPC ................. 250/338.1, 338.5, 339.06, 339.13, 250/341.1, 341.2, 459.1, 493.1, 504 R
See application file for complete search history.

(56) References Cited

U.S. PATENT DOCUMENTS

2009/0207413 A1    8/2009 Carpenter et al.

OTHER PUBLICATIONS

European Search Report dated Jun. 29, 2012 for European Patent Application No. 11250881.7.
S. E. Han et al., "Beaming Thermal Emission from Hot Metallic Bull's Eyes," Optics Express, vol. 18, No. 5, Mar. 1, 2010.
Ming-Wei Tsai et al., "High Perforrmance Midinfrared Narrow-Band Plasmonic Thermal Emitter," Applied Physics Letters, American Institute of Physics, Melville, NY, vol. 89, No. 17, Oct. 25, 2006.
Saves Tay, et al., Plasmonic Thermal IR Emitters Based on Nanoamorphous Carbon, Applied Physics Letters, AIP, American Institute of Physics, Melville, NY, vol. 94, No. 7, Feb. 20, 2009.
Rogers, P.H. et al., Au-(Y2O3)X(ZrO2)1-X Thin Films for High Temperature Gas Detection via Changes in Optical Absorption: Interfacial Influences on Metallic Nanoparticle Optical Properties, Sensors, 2007, IEEE, IEEE, PI, Oct. 28, 2007, pp. 415-418.
Sirinakis, George et al., "Development and Characterization of Au-YSZ Surface Plasmon Resonance Based Sensing Materials: High Temperature Detection of CO," The Journal of Physical chemistry B, vol. 110, No. 27, Jul. 1, 2006, pp. 13508-13511.
Rogers, R.H., et al., "Au-(Y2O3)X(Zr0)1-X Thin Films as an All-Optical Method for Measuring Emissions at High Temperatures," Sensors, 2007.

*Primary Examiner* — Mark R Gaworecki
(74) *Attorney, Agent, or Firm* — Edwards Wildman Palmer LLP; Scott D. Wofsy; Christopher J. Cillié

(57) ABSTRACT

A probe assembly for measuring the concentration of exhaust's emissions in a turbine engine. The probe assembly including a first probe member configured and operable to passively generate a beam of light wherein the wavelength of the beam of light is contingent upon the configuration of the first probe member. A second probe member positioned in the probe assembly to receive the beam of light generated by the first probe member, the second probe member configured and operable to attenuate the light passively generated from the first probe member contingent upon the gaseous species present in the exhaust emissions of the turbine engine.

20 Claims, 5 Drawing Sheets

PASSIVE OPTICAL GASEOUS EMISSIONS SENSOR

CROSS-REFERENCE TO RELATED APPLICATIONS

This application claims priority to U.S. patent application Ser. No. 61/409,294 filed Nov. 2, 2010, which is incorporated herein by reference in its entirety.

FIELD OF THE INVENTION

The subject invention is directed to gas turbine engines, and more particularly, to a sensor for measuring the concentration of exhaust emissions in a gas turbine engine.

BACKGROUND OF THE INVENTION

To achieve peak operating performance and efficiency of a gas turbine engine, it is advantageous to detect, in real time, the gaseous content present in the emissions of a gas turbine engine. For instance, detection of nitrogen oxide and/or the carbon dioxide concentrations present in exhaust emissions of a gas turbine is beneficial so as to tune/adjust the gas turbine engine towards peak performance. However, current technology for measuring exhaust emissions in a gas turbine engine is unable to provide real time measurements and is also often too large to be positioned in the confines of the exhaust flow path of a gas turbine engine.

The harsh environment of the exhaust flow path has proven to be a deterrent for the introduction of any such measuring device principally due to the extreme operating temperatures present in the exhaust chamber. Clearly, there is a need in the art for a measurement system and sensor that provides real time measurement and detection for the exhaust emissions of a gas turbine engine that can withstand the harsh environment of the exhaust flow path in a gas turbine engine.

SUMMARY OF THE INVENTION

In one aspect, a probe assembly is described in which an aspect of the invention is for measuring the concentration of exhaust emissions in a turbine engine using a passive sensor.

The probe assembly preferably includes a first probe member configured and operable to generate a beam of light wherein the wavelength of the beam of light is contingent upon the configuration of the first probe member. Also included is a second probe member positioned in the probe assembly to receive the beam of light generated by the first probe member, the second probe member configured and operable to attenuate the light generated from the first probe member at a peak absorption wavelength contingent upon the gaseous species present in the exhaust emissions of the turbine engine.

In further, optional aspects, the foregoing probe assembly can include a first probe sub assembly including a first probe member configured and operable to generate a beam of light wherein the intensity of the beam of light is contingent upon the temperature of the emissions of the gas turbine engine. A second probe member is positioned in the first probe sub assembly to receive the beam of light generated by the first probe member, the second probe member configured and operable to attenuate light received from the first probe member contingent upon the concentration of a gaseous species present in the exhaust emissions of the turbine engine. In addition to the aforesaid first probe sub assembly, a second probe sub assembly is provided which includes a third probe member configured and operable to generate a beam of light wherein the intensity of the beam of light is contingent upon the temperature of the third probe member. The probe assembly further includes a photodiode assembly that detects light emitted from each of the first and second probe subassemblies wherein the detected light signal received from the third probe member is utilized as a correction signal for the detected light signal from the second probe member so as to correct for temperature and contamination effects to the light emitted from the first probe sub assembly.

BRIEF DESCRIPTION OF THE DRAWINGS

The objects and features of the invention can be understood with reference to the following detailed description of an illustrative embodiment of the present invention taken together in conjunction with the accompanying drawings in which.

WRITTEN DESCRIPTION OF CERTAIN EMBODIMENTS OF THE INVENTION

The present invention is now described more fully with reference to the accompanying drawings, in which an illustrated embodiment of the present invention is shown wherein like reference numerals identify like elements. The present invention is not limited in any way to the illustrated embodiment as the illustrated embodiment described below is merely exemplary of the invention, which can be embodied in various forms, as appreciated by one skilled in the art. Therefore, it is to be understood that any structural and functional details disclosed herein are not to be interpreted as limiting, but merely as a basis for the claims and as a representative for teaching one skilled in the art to variously employ the present invention. Furthermore, the terms and phrases used herein are not intended to be limiting but rather to provide an understandable description of the invention.

The subject invention is directed to a new and useful system for passively measuring the concentration of exhaust emissions in the emissions flow path of a gas turbine engine. The system includes at least one passive probe assembly for measuring gaseous emissions within the emissions flow path for observing emissions characteristics within the emissions chamber.

Preferably, the subject invention system transmits blackbody infrared radiation that is surrounding a probe assembly to a light detecting component, such as a photodiode through certain light modifiers. It is to be appreciated, as used throughout this specification, the term "light" is to encompass light wavelengths which fall into the visible coherent spectrum and non-visible spectrum (such as infrared light wavelengths).

As discussed further below, a first light modifying component (e.g., a first probe component 10) is preferably a light emitting component that preferably defines a narrow spectrum bandwidth producing light having a collimated beam that is suitable for a focused input to fiber optics. It is to be appreciated and understood that this first probe component is configured and operable to preferably emit light, such as infrared (IR) radiation at an intensity based upon its black body temperature. Thus, the higher the temperature, the greater its radiation intensity. Further, it is to be appreciated the first probe component 10 emits a constant wavelength which may be tuned to a desired absorption wavelength for the maximum intensity for a temperature range with regards to a second probe component 24 preferably having a nanoparticle (NP) thin film as discussed further below. It is to be also appreciated that the radiated power generated by the first probe component 10 is to be proportional to its surface.

In the illustrated embodiment, it is desirable to isolate the first probe component 10 from the atmosphere so as to prevent oxidation of metal films used to generate plasmons for emitting light therefrom. One such way to achieve this is to passivate the aforesaid metal films with a deposited dielectric film (such as, silicon oxide, silicon nitride, aluminum oxide or other refractory films) which is also pinhole free. Another way to isolate the first probe component 10 from the atmosphere is to use an encapsulation structure in which the substrate supporting the first probe member 10 is mated to a similar substrate preferably through direct fusion bonding or via a metallurgical bond. For instance, such a fusion bond could be a sapphire to sapphire bond as described in U.S. Pat. No. 5,349,492 incorporated herein in its entirety. Additionally, a metallurgical bond may be used as described in U.S. Pat. No. 7,642,115 also incorporated herein in its entirety.

A second light modifying component (e.g., a second probe component 24) is preferably provided which is responsive to the gaseous emissions of the gas turbine engine, preferably using principals of absorption spectrography to detect spectral shifts. In accordance with an illustrated embodiment of the invention, the second probe component uses a nano-particle thin film having a relatively low Q absorption band peak. In other words, the peak of the second probe component shifts in frequency according to the gas concentration, species content and temperature present in the emissions of the gas turbine engine. Additionally, the amplitude of the (negative) peak of the second probe component will change based on the amount of radiation intensity that excites the second probe component.

Figure 1:
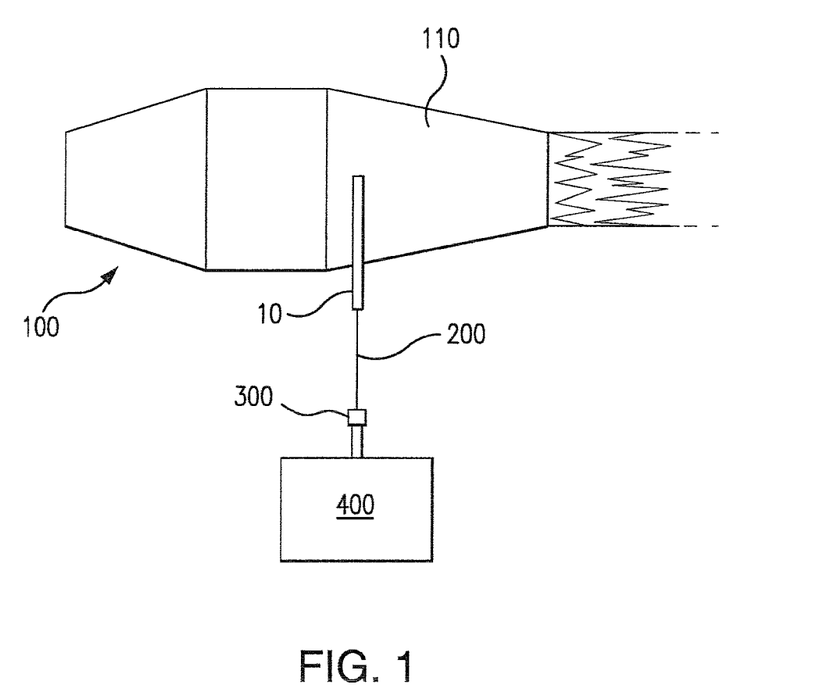
FIG. 1 is a schematic overview of an illustrated embodiment for a probe assembly of the subject invention.

In accordance with an illustrated embodiment of the subject invention, and as shown in FIG. 1, a probe assembly, designated generally be reference numeral 10, is shown disposed in the exhaust flow path 110 of a gas turbine engine, shown generally by reference numeral 100. A fiber optic strand 200 preferably couples probe assembly 10 to a photodiode component 300. Photodiode component 300 is preferably coupled to an electronic analysis system 400 for providing real-time measurements of the exhaust emissions for a gas turbine engine 100 using gaseous emissions detection of the passive probe assembly 10.

Figure 2:
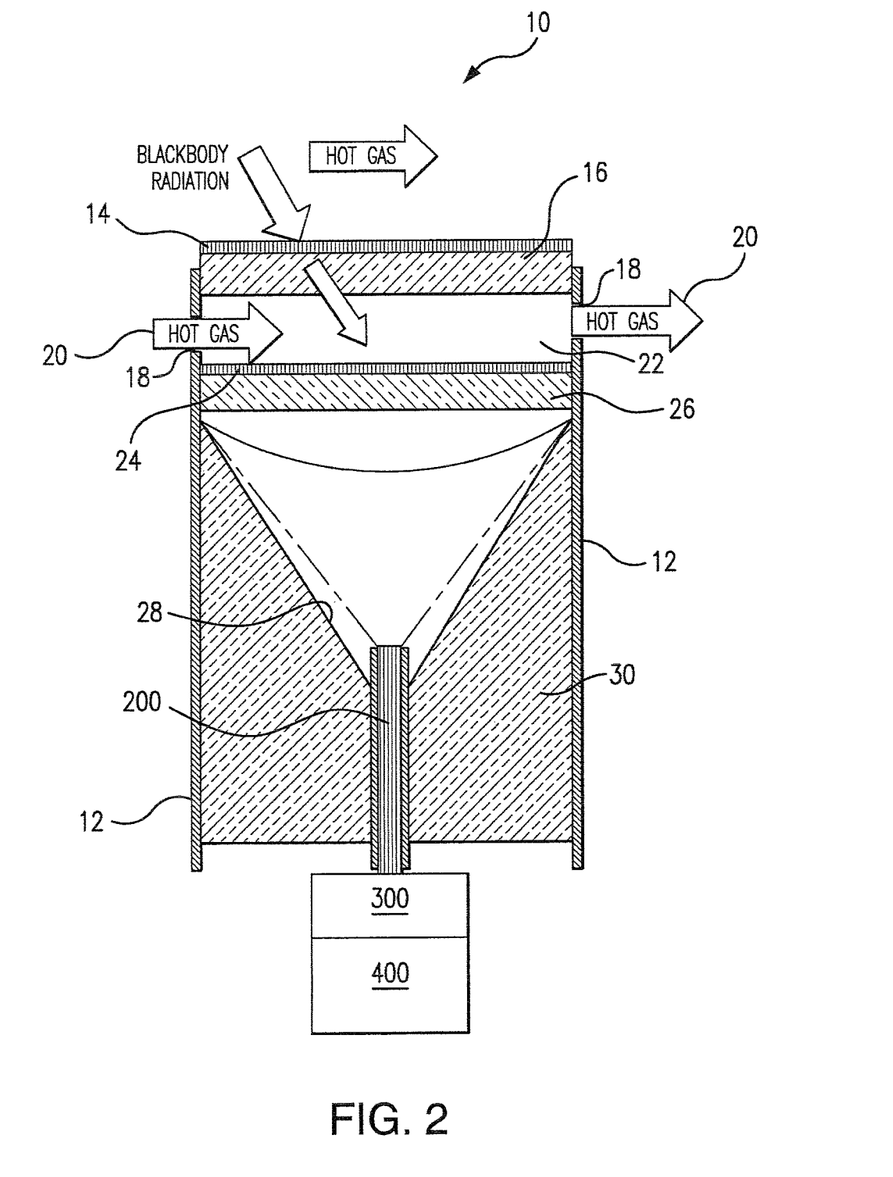
FIG. 2 is a schematic overview of a probe member used in the probe assembly of FIG. 1.

With reference now to FIG. 2 (and with continuing reference to FIG. 1), probe assembly 10 consists of outer housing 12 preferably formed by metalizing and brazing the below described substrates of the probe assembly 10 into a metal package or support structure such as that described in U.S. Pat. No. 7,642,115 incorporated herein in its entirety. It is to be understood, the probe assembly 10 is configured to withstand the high temperatures present in the emissions flow path 110 of a gas turbine engine 100. Provided on a first end of the probe assembly 10 is a first probe component 14 generally configured and operable to passively generate a beam of light caused by thermal excitation of surface plasmons present on the first probe component 14. A lens assembly 16 is preferably provided adjacent the first probe component 14, preferably formed of sapphire or a quartz acromate lens. It is to be appreciated lens assembly 16 focuses the beam of light generated by the first probe component 14.

As shown in FIG. 2, the outer housing 12 is provided with cutout portions 18 for permitting gaseous emissions 20 of gas turbine engine 100 to pass through an inner chamber portion 22 of the housing 12 for the probe assembly 10. As described below, these gaseous emissions 20 are to chemical react with a second probe component 24 as described below.

Provided in spaced proximity from the first probe component 14 and lens assembly 16 is a second probe component 24 generally configured and operable to receive the beam of light emitted by the first probe component 14 and to attenuate, or more generally, modulate, received light at a peak absorption wavelength contingent upon the gaseous species present in the exhaust emissions 20 of the turbine engine 100 passing through the inner chamber portion 22 of the probe assembly 10. To put otherwise, it is to be appreciated that the second probe component 24 is to have light modulating qualities varying from opaque to transparent contingent upon the gaseous species present in the exhaust emissions 20 of the turbine engine 100. In the illustrated embodiment, this second probe member 24 is preferably a chemical sensor that is compatible with the harsh operating environment present in the emissions flow path 110 of a gas turbine engine wherein temperatures can range between 500-1000° C. In the illustrated embodiment, the second probe member 24 is preferably formed of nanocomposite materials containing Au nanoparticles (NP) embedded in a $Y_2O_3$ stabilized $ZrO_2$ (YSZ) matrix. Preferably upon exposure to high temperatures and air, $O^-$ ions are formed within the matrix whereby CO, $H_2$ and $NO_2$ present in the gas emissions 20 of a turbine engine 100 catalytically react with $O^-$ ions at the Au—YSZ interface so as to alter the light transmitting qualities of the second probe member 24 so as to attenuate light generated from the first probe component 14 passing therethrough. Simply put, the second probe member 24 becomes "activated" upon the presence of certain species in the emissions of the gas turbine engine 100, such as carbon dioxide, nitrogen dioxide and other hydrocarbon chemicals in addition to the temperature of the aforesaid emissions. That is, the second probe member transitions so as to have translucent light transmitting qualities contingent upon the presence of certain chemical compounds and the temperature present in the emissions in a gas turbine engine 100.

A second lens assembly 26 is preferably provided adjacent the second probe component 24, preferably formed of sapphire or a quartz acromate lens. It is to be appreciated the second lens assembly 26 focuses the beam of light passing through and attenuated by the second probe component 24. Provided and formed adjacent the second lens assembly 26 in the probe assembly 10 is a low emissivity surface 28 leading to the fiber optic strand 200. Preferably disposed in the probe assembly 10 intermediate the low emissivity surface 28 and its outer housing 12 is a material filler 30 capable of withstanding the aforesaid high temperature environment of the emissions flow path 110 of the gas turbine engine 100.

Figure 5:
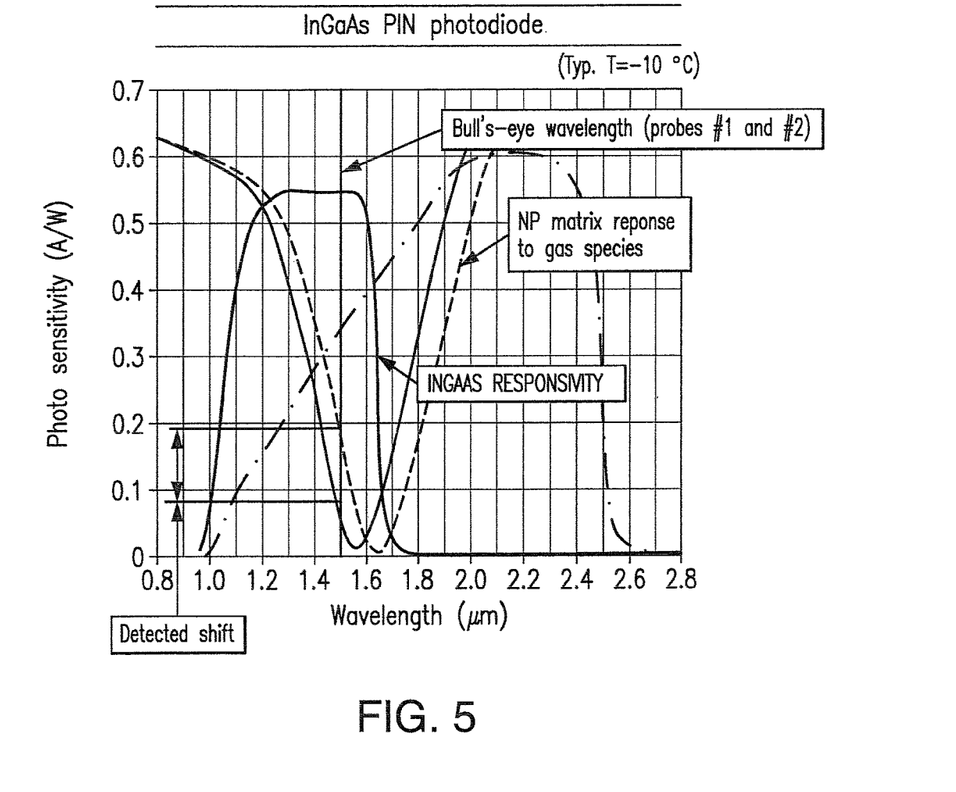
FIG. 5 is a graph depicting absorption peak shifts and wavelength emissions.

With continuing reference to FIGS. 1 and 2, and in accordance with the illustrated embodiment, it is to be understood the first probe component 10 is preferably tuned to the frequency of the absorption peak of the NP(nano-particles) layer of the second probe component 24 such that a narrow band of photons impinge on the NP layer heated surface of the second probe component 24. The NP layer of the second probe component 24 preferably generates plasmons which have a change in resonant frequency based on their size and matrix interface oxygen content, which in turn, is affected by the species being detected present in the emissions flow path 110 of a gas turbine engine 100. Preferably, it is to be understood that in the illustrated embodiment infrared (IR) photons that pass through the outer coating of the NP layer of the second probe component 24 are excited at the resonant frequency of the first probe member 14 which is tuned to a peak absorption wavelength of choice. That is, the gaseous species that affects the NP matrix on the sensor surface of the second probe component 24, will affect the photon absorption and shift the absorption peak of the second probe component 24. With reference now to FIG. 5, as the absorption peak shifts and the wavelength emitted by the first probe member 14 remains constant, more or less photons will be absorbed by the NP layer of the second probe component 24 depending on how much the absorption peak deviates from the peak of the first probe member 14.

With regards to the illustrated embodiment shown in FIGS. 1 and 2, the light emission of the first probe component 14 as attenuated by the NP layer of the second probe component 24 is transmitted from the fiber optic strand 200 to an absorption spectrometer, such as a photodiode component 300 and associated circuitry. Preferably coupled to the photodiode component 300 is an analysis system 400 configured and operable to correlate peak to species and/or the species concentration of the gaseous emissions 20 in the emissions flow path 110 of a gas turbine engine 100. This data in turn may be used by the control systems of the aircraft to determine operating performance and efficiency of the gas turbine engine 100 as well as to adjust the operation of the gas turbine engine 100 to achieve peak operating performance and efficiency.

Figure 3:
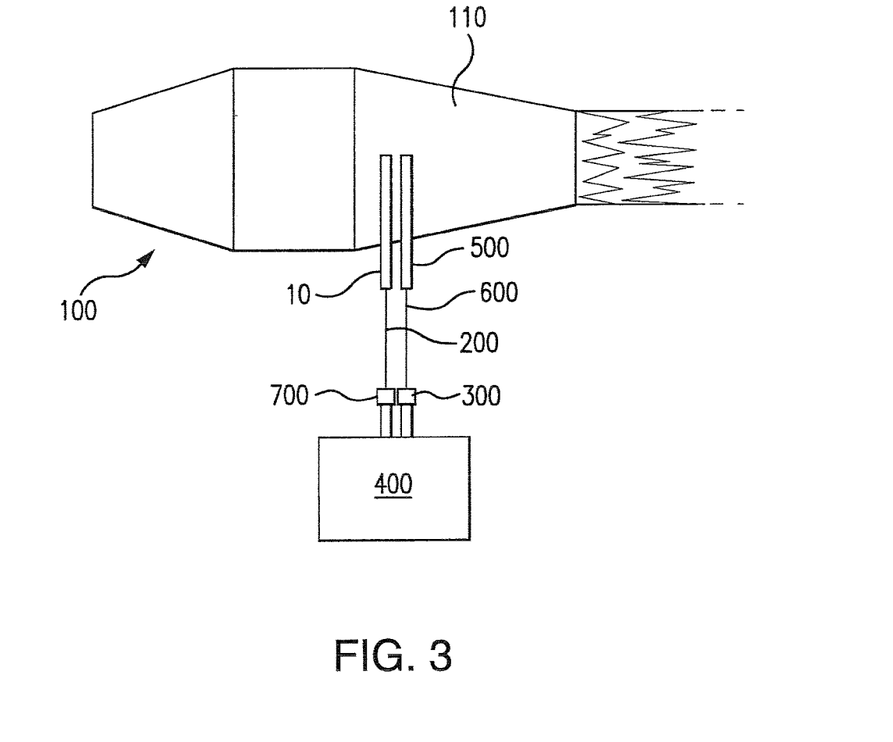
FIG. 3 is a schematic overview of another illustrated embodiment for a probe assembly of the subject invention.
Figure 4:
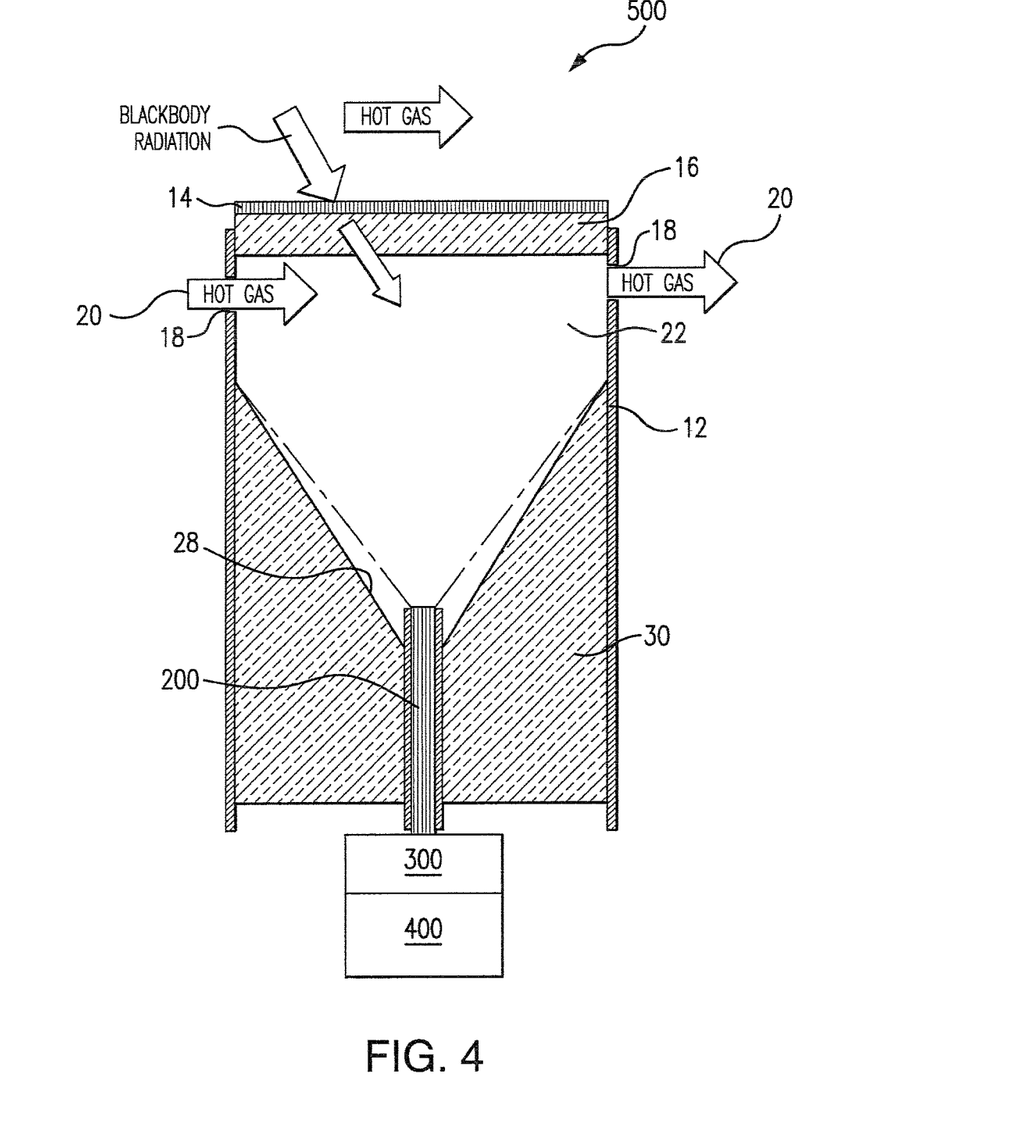
FIG. 4 is a schematic overview of a second probe member used in the probe assembly of FIG. 3.

With a first illustrated embodiment of the subject invention shown and described above with reference to FIGS. 1 and 2, reference is now made to FIGS. 3 and 4, wherein another illustrated embodiment of the subject invention is provided to which it is appreciated that for a passive infrared powered system, such as the subject invention, the temperature variation and/or light path contamination present in the emissions flow path 110 of a gas turbine engine 110 typically causes errors. The subject invention corrects for such variation in output by providing a second probe assembly (e.g., probe assembly 500), which is preferably identical to the first probe assembly 10, except for only including a first light modifying component, as described further below. Therefore, the intensity of light provided from the second probe assembly 500 will be related to radiation intensity present in the emissions flow path 110 of a turbine engine 100 to provide a correction signal for the first probe assembly 10. It is also to be understood and appreciated that the aforesaid correction signal also has utility for determining the gas species and concentration present in the emissions of the gas turbine engine.

Therefore, as shown in FIGS. 3 and 4, is another illustrated embodiment of the subject invention. Wherein like reference numerals indicate like elements, and as mentioned above, the illustrated embodiment of FIGS. 3 and 4 is substantially similar to the illustrated embodiment of FIGS. 1 and 2 with the exception of the inclusion of a second probe assembly 500.

With regards to the second probe assembly 500 it is substantially identical to the first probe assembly 10 except for the omission of the second probe component 24 and the second lens assembly 26. It is to be understood the first probe component 14 of the second probe assembly 500, is preferably tuned to the same wavelength as the first probe component 14 of the first probe assembly 10 but it will not have the plasmon generating NP matrix of the second probe component 24 and thus is to only detect IR radiation from the blackbody radiation present in the emissions flow path 110 of the gas turbine engine 100.

As illustrated in FIG. 3, a fiber optic strand assembly 200 couples the output of the first probe assembly 10 to preferably photodiode component 300, which in turn is coupled to an analysis system 400. With regards to the second probe assembly 500, a fiber optic strand assembly 600 couples its output to preferably a photodiode component 700 which is also coupled to analysis system 400. It is to be understood, output from the second probe assembly 500 is used to correct the output of the first probe assembly 10 due to temperature and contamination effects on radiation intensity in the emissions flow path 110 of a gas turbine engine 100. The analysis system 400 is preferably calibrated based on the output from the first probe assembly 10, based on known concentrations of the gaseous species in the emissions flow path 110 being detected. Therefore, it is to be understood the temperature of preferably a tip portion of the first and second probe assemblies 10, 500 are measured to ensure the readings are corrected back to a known calibration. The analysis system 400 preferably includes comparator circuitry to provide calibration curves for the respective inputs of probe assemblies 10 and 500 as well as providing temperature correction based on the input of the second prove assembly 500.

Optional embodiments of the present invention may also be said to broadly consist in the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth.

Although illustrated embodiments of the present invention has been described, it should be understood that various changes, substitutions, and alterations can be made by one of ordinary skill in the art without departing from the scope of the present invention.

What is claimed is:

1. A probe assembly for measuring the concentration of exhaust emissions in a turbine engine, the probe assembly comprising:
    a first probe member configured and operable to generate a beam of light of constant wavelength upon thermal excitation of a component thereof, wherein the wavelength of the beam of light is contingent upon the configuration of the first probe member; and
    a second probe member positioned in the probe assembly to receive the beam of light generated by the first probe member, the second probe member configured and operable to absorb and attenuate the light generated from the first probe member with a peak absorption frequency that varies in accordance with the gaseous species present in the exhaust emissions of the turbine engine,
    wherein the constant wavelength of the first probe member is tuned to the peak absorption frequency of the second probe member so that more or less photons will be absorbed by the second probe member depending on how much of the gaseous species is present in the exhaust.

2. A probe assembly for measuring the concentration of exhaust emissions in a turbine engine as recited in claim 1, further including a photodiode assembly that detects the light attenuated from the second probe member.

3. A probe assembly for measuring the concentration of exhaust emissions in a turbine engine as recited in claim 2, wherein the photodiode assembly includes at least one fiber optic strand.

4. A probe assembly for measuring the concentration of exhaust emissions in a turbine engine as recited in claim 2, wherein the photodiode assembly is coupled to an analysis system located remotely from the first and second probes, the analysis system configured and operable to determine species concentration of the exhaust emissions of the turbine engine.

5. A probe assembly for measuring the concentration of exhaust emissions in a turbine engine as recited in claim 2, wherein the second probe member attenuates light emission from the first probe member prior to detection by the photodiode.

6. A probe assembly for measuring the concentration of exhaust emissions in a turbine engine as recited in claim 1, wherein the first probe member includes a metallic substrate configured to be operable in a thermal process to emit light.

7. A probe assembly for measuring the concentration of exhaust emissions in a turbine engine as recited in claim 6, wherein the first probe member emits a single wavelength tunable to a desired wavelength for maximum intensity in the wavelength required for the second probe member.

8. A probe assembly for measuring the concentration of exhaust emissions in a turbine engine as recited in claim 6, wherein the first probe member is operable to emit a focused beam of light having a defined spectral bandwidth suitable for input to a fiber optic strand.

9. A probe assembly for measuring the concentration of exhaust emissions in a turbine engine as recited in claim 1, wherein the second probe member consists of a nanoparticle thin film substrate having a prescribed infrared absorption band peak.

10. A probe assembly for measuring the concentration of exhaust emissions in a turbine engine as recited in claim 9, wherein the light absorption band peak of the second probe member shifts in wavelength contingent upon presence of a specific gas at a particular concentration in the exhaust emissions of the turbine engine.

11. A probe assembly for measuring the concentration of exhaust emissions in a turbine engine as recited in claim 9, wherein the light absorption band peak of the second probe member shifts in wavelength contingent upon the species of the exhaust emissions of the turbine engine.

12. A probe assembly for measuring the concentration of exhaust emissions in a turbine engine as recited in claim 9, wherein the amplitude of the absorption band peak changes are detected contingent upon an intensity level of light emitted from the first probe member after light intensity is corrected for using the second probe.

13. A probe assembly for measuring the concentration of exhaust emissions in a turbine engine as recited in claim 9, wherein the nanoparticle thin film substrate of the second probe member consists of a metal matrix having nanoscale gold precipitates configured to generate plasmons.

14. A probe assembly for measuring the concentration of exhaust emissions in a turbine engine as recited in claim 1, wherein the first probe member is tuned to a wavelength to correlate with the absorption band peak of the second probe member.

15. A probe assembly for measuring the concentration of exhaust emissions in a turbine engine as recited in claim 1, wherein the beam of light generated from the first probe member is in the visible light spectrum.

16. A probe assembly for measuring the concentration of exhaust emissions in a turbine engine as recited in claim 1, wherein the beam of light generated from the first probe member is in the infrared light spectrum.

17. A probe assembly for measuring the concentration of exhaust emissions in a turbine engine, the probe assembly comprising:
a first probe subassembly including:
a first probe member configured and operable to generate a beam of light at a constant wavelength upon thermal excitation of a component thereof, wherein the intensity of the beam of light is contingent upon the temperature of the first probe member; and
a second probe member positioned in the first probe assembly to receive the beam of light generated by the first probe member, the second probe member configured and operable to absorb and attenuate light received from the first probe member with a peak absorption frequency that varies in accordance with gaseous species present in the exhaust emissions of the turbine engine;
wherein the constant wavelength of the first probe member is tuned to the peak absorption frequency of the second probe member so that more or less photons will be absorbed by the second probe member depending on much of the gaseous species is present in the exhaust;
a second probe subassembly including a third probe member configured and operable to generate a beam of light, wherein the intensity of the beam of light is contingent upon the temperature of the third probe member; and
a photodiode assembly that detects light emitted from each of the first and second probe subassemblies, wherein the detected light signal received from the third probe member is utilized as a correction signal for the detected light signal from the second probe member so as to correct for temperature and contamination effects relative to the radiation intensity emitted from the first probe subassembly.

18. A probe assembly for measuring the concentration of exhaust emissions in a turbine engine as recited in claim 17, wherein the photodiode assembly is coupled to an analysis system located remotely from the first and second probe subassemblies, the analysis system configured and operable to determine species concentration of the exhaust emissions of the turbine engine.

19. A probe assembly for measuring the concentration of exhaust emissions in a turbine engine as recited in claim 17, wherein the analysis system is configured to utilize a comparator method using the detected signal received from the third probe member to detect a shift in an absorption curve wavelength of the second probe member.

20. A method of forming a probe assembly for detecting infrared radiation in a turbine engine for measuring the concentration of exhaust emissions in the turbine engine, the method comprising:
providing a first probe member configured and operable to generate a beam of light at a constant wavelength, wherein the intensity of the beam of light is contingent upon the temperature of the first probe member, wherein the first probe member includes a metallic substrate configured to be operable in a thermal process to emit infrared radiation in response to heat; and
providing a second probe member positioned in the probe assembly to receive the beam of light generated by the first probe member, the second probe member configured and operable to absorb attenuate the beam of light from the first probe member contingent upon the gaseous species present in the exhaust emissions of the turbine engine, wherein the second probe member consists of a nanoparticle thin film substrate having a prescribed infrared absorption band peak, and wherein the constant wavelength of the first probe member is tuned to the infrared absorption band peak.

* * * * *